United States Patent
Gurin

(10) Patent No.: US 10,640,713 B1
(45) Date of Patent: May 5, 2020

(54) BIOMASS ENERGY AND VALUE MAXIMIZATION

(71) Applicant: Michael H Gurin, Glenview, IL (US)

(72) Inventor: Michael H Gurin, Glenview, IL (US)

(*) Notice: Subject to any disclaimer, the term of this patent is extended or adjusted under 35 U.S.C. 154(b) by 205 days.

(21) Appl. No.: 15/909,567

(22) Filed: Mar. 1, 2018

(51) Int. Cl.
| | | |
|---|---|---|
| *C10G 7/08* | (2006.01) | |
| *C10G 7/04* | (2006.01) | |
| *C10G 7/12* | (2006.01) | |
| *B01D 11/04* | (2006.01) | |
| *G16C 99/00* | (2019.01) | |
| *C08L 97/00* | (2006.01) | |
| *C08L 97/02* | (2006.01) | |
| *C08L 1/02* | (2006.01) | |

(52) U.S. Cl.
CPC ............ *C10G 7/08* (2013.01); *B01D 11/0492* (2013.01); *C10G 7/04* (2013.01); *C10G 7/12* (2013.01); *G16C 99/00* (2019.02); *B01D 2253/1124* (2013.01); *C08L 1/02* (2013.01); *C08L 97/005* (2013.01); *C08L 97/02* (2013.01); *C10G 2300/1011* (2013.01); *C10L 2290/02* (2013.01)

(58) Field of Classification Search
CPC ........................................................ F02C 6/18
USPC ........ 585/240–242; 60/39.52–39.5, 645, 659
See application file for complete search history.

(56) References Cited

U.S. PATENT DOCUMENTS

| | | | |
|---|---|---|---|
| 8,623,102 B2* | 1/2014 | Quignard | C10G 1/08 44/307 |
| 9,249,018 B2* | 2/2016 | Gurin | C01B 3/22 |
| 2016/0002851 A1* | 1/2016 | Gates | D21C 1/00 530/507 |
| 2018/0016355 A1* | 1/2018 | Nelson | C08H 8/00 |
| 2018/0142162 A1* | 5/2018 | Lin | C10G 1/065 |

\* cited by examiner

*Primary Examiner* — Nina Bhat

(57) ABSTRACT

A system and method to a power production cycle optimized for combusting fractionated solid biomass such that the fractionated solid biomass is transported in a solvent that is utilized in a solvent-enhanced biomass liquefaction conversion process and the solvent is subsequently fractionated from the fractionated solid biomass for direct use as a liquid fuel for transport vehicles to maximize energy density and total system energy efficiency. Utilizing the solvent as a waste heat recovery method prior to combustion by the transport vehicle increases the total system energy efficiency and maximizes biomass value creation.

19 Claims, 4 Drawing Sheets

Fig. 4

Object ID

| Electricity Fuel Consumption Historic f(t) | Electricity Fuel Consumption Projected f(t) | Electricity Fuel Revenue Historic f(t) | Electricity Fuel Revenue Projected f(t) |
|---|---|---|---|
| Flow Battery Consumption Historic f(t) | Flow Battery Consumption Projected f(t) | Flow Battery Revenue Historic f(t) | Flow Battery Revenue Projected f(t) |
| Vehicle Fuel Consumption Historic f(t) | Vehicle Fuel Consumption Projected f(t) | Vehicle Fuel Revenue Historic f(t) | Vehicle Fuel Revenue Projected f(t) |
| Biomass Consumption Historic f(t) | Biomass Consumption Projected f(t) | Biomass Revenue Historic f(t) | Biomass Revenue Projected f(t) |
| Biomass Decomposition Temperature | Biomass Energy Density | Biomass Particle Size | Biomass Solvent Solubility |
| Transport Projected Temperature | Solvent Consumption Historic f(t) | Solvent Consumption Projected f(t) | Power Generation Parameters |
| Biomass Fractionation Parameters | Solvent Physical Parameters | Solvent Consumption Projected f(t) | Production Equipment Parameters |
| Secondary Process Parameters e.g., Gasifier | Metal Oxide & Ferrite Physical Parameters | Solvent Consumption Projected f(t) | Logistics Equipment Parameters |

BIOMASS ENERGY AND VALUE MAXIMIZATION

FIELD OF INVENTION

The invention relates to methods for converting and maximizing lignocellulosic biomass materials into smaller fractionated biomass particles through a solvent-solid solution or slurry and subsequent use of the then fractionated solvent as a liquid transportation fuel to maximize solvent value and to minimize the fuel costs of for operating an integrated power generator by minimizing the energy content of fractionated solvent within the total power generator fuel such that the solvent is first a carrier of the smaller fractionated biomass particles/components and then secondly a mobile liquid transportation fuel for a transport vehicle.

BACKGROUND OF INVENTION

Biomass is the only renewable source of carbon on earth and what is termed "lignocellulosic biomass" or "woody biomass"—material composed almost exclusively of the distinct polymers cellulose, hemicellulose, lignin, and lignocellulose—is the most abundant form of biomass. It is estimated that $1.3 \times 10^{12}$ kg/yr of these materials could be sustainably produced in the United States without compromising the supply of building materials or food. As of April, 2005 production of these materials was roughly $1.8 \times 10^{11}$ kg/yr in the United States.

Historically there are three approaches to the production of liquid fuels and commodity chemicals from woody biomass: gasification, pyrolysis, or hydrolysis. Pyrolysis and gasification involve heating raw biomass to select for either liquids or gases, respectively. They are non-selective processes. They are attractive because they produce a ready-to-go product (in poor yield) such as "bio-oil" or syn gas, the latter of which is attractive because of the large chemical infrastructure already in place for its utilization. However, both processes produce a large quantity of char, which has been described as "the most cumbersome and problematic parameter in any gasification commercialization effort." Furthermore, the production of syn-gas "syngas" for subsequent conversion to liquid fuels has proven to not be as modular or scalable suitable for community-based systems.

Hydrolysis refers to the specific efforts to use near- and supercritical water to convert cellulose and hemicellulose to fermentable sugars and assumes that the lignin thus produced will be treated separately. The problems with hydrolysis are two-fold: water must be separated from the final product, and the chemical bonds that compose woody biomass, especially aryl ethers, are inherently resistant to hydrolysis.

A need to maximize the value extraction from biomass, while minimizing the system costs and energy consumption for processing and transporting the biomass, is required such that the biomass treatment process leverages virtually all aspects of the processing and transporting of the biomass through the highest value-add consumption of virtually all constituents.

SUMMARY OF INVENTION

It is an object of the invention to maximize the system energy efficiency of the biomass to fuel conversion process with a primary method of reducing thermal losses associated with removing solvent from cellulose and/or lignin.

It is yet another object of the invention to maintain the cellulose and/or lignin in a pump-able solution or slurry (i.e., to avoid handling of powder or solids).

Another object of the invention is to eliminate (or greatly reduce) the transportation costs and energy consumption associated with return of solvent when the transportation of the solvent with cellulose and/or lignin after solvent removal from the cellulose and/or lignin in which the cellulose and/or lignin are consumed in the relatively lower value (as compared to transportation liquid fuels) production of electricity.

It is another object of the invention such that the pump-able solution or slurry of solvent with at least one of cellulose or lignin is mixed with a metal oxide for highly efficient and homogeneous production of syngas for electricity production such that the solvent is evaporated at a temperature lower than the metal oxide and/or metal ferrite production/yield of oxygen which then in turn at least partially combustsireacts with the cellulose, hemicellulose, or lignin (and any byproducts or coproducts) to create syngas. It is a further object of the invention such that syngas is largely absent of nitrogen enabling an otherwise higher calorific syngas thus capable of having higher thermodynamic cycle efficiencies attributed to the higher combustion temperatures.

It is yet another object of the invention for $Mg(OH)_2$ to be further incorporated with the solvent slurry/solution composition, in which the $Mg(OH)_2$ or other known compounds that undergo carbonation has absorption of $CO_2$, to achieve an enhanced water-gas-shift reaction at a temperature above 150 C, such that the solvent is fully evaporated and separated from the then remaining homogeneously dispersed fractionated solid biomass constituents (i.e., cellulose, or lignin fractions) prior to any $Mg(OH)_2$ reactions. The cellulose and lignin are fundamentally different molecules and therefore their reaction kinetics are also very different.

It is a further object of the invention that the formation of char and/or tar is minimized by leveraging the prior fractionation of biomass into its constituents cellulose, hemicellulose, and lignin and the subsequent gasification by maintaining the separation of the constituents (as well as any byproducts or coproducts produced) in the gasifier (i.e., gasification of cellulose, hemicellulose, and lignin are preferably in individual gasifiers) as each constituent has a different rate of disassociation.

It is yet another object of the invention such that electricity produced is stored in a flow battery that releases oxygen during the charging of the flow battery electrolyte. Therefore, the cost of oxygen (as well as energy requirements) otherwise required for syngas is significantly deferred (preferably the production of oxygen in traditional (i.e., non-flow battery electrolyte charging).

Yet another object of the invention is to have the availability of an oxygen generator that can be rapidly started or shutdown, such that the rate of startup or shutdown is less than 10 minutes, preferably less than 2 minutes, and particularly preferred less than 30 seconds without (i.e., void) of thermal-cycling concerns or limitations.

The system creates a fundamental integration of multiple processes to maximize the total efficiency and reduce wasted heat and chemical products as much as possible.

BRIEF DESCRIPTION OF DRAWINGS

FIG. 4 is a chart depicting a subset of the system parameters utilized within the overall management and control system.

DEFINITIONS

Figure 1:
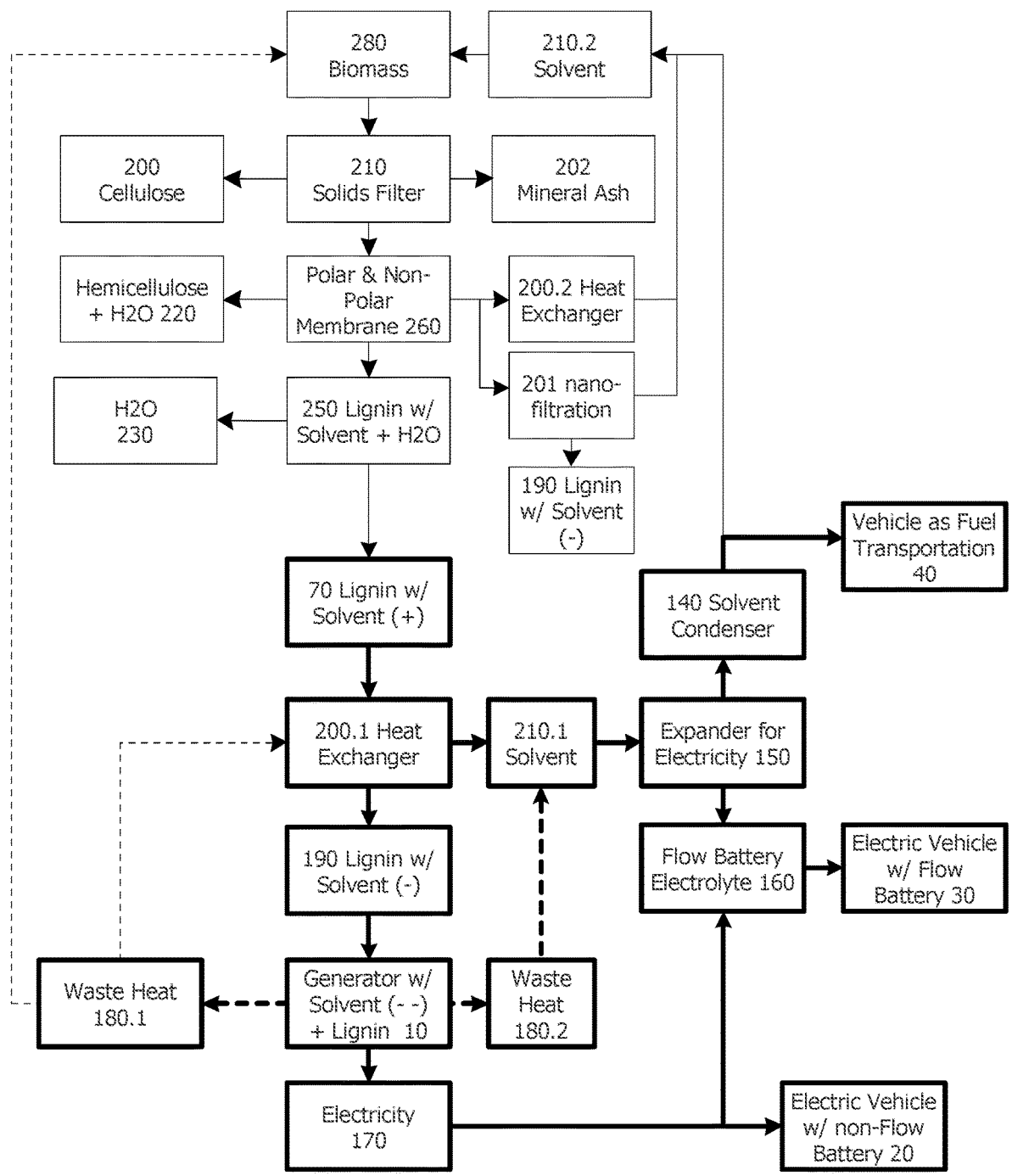
FIG. 1 is a flow chart detailing the system from a solvent centric perspective within a distributed environment, such that the biomass liquefaction and fractionation process is at a central location and at least a partial solvent separation takes place after being transported to a distributed location having electricity power generation.

The term "synthesis gas," also referred to as "syn-gas" or "syngas" refers to a mixture of hydrogen (H2), carbon monoxide (CO), carbon dioxide (CO2), and methane (CH4).

The term "biomass" is any biological material derived from living or recently living organisms. This material can be converted into useful energy as known in the art, preferably in the form of liquid fuels via biomass to liquid conversion process.

The term "liquid fuel" is combustible or energy-generating molecules that can be harnessed to create mechanical or kinetic energy. In this embodiment, liquid fuels are preferably created from biomass to be used in place of traditional gasoline/diesel transportation fuels, known as "biofuels."

The following lists chemical names and their respective symbols for clarity: magnesium hydroxide (Mg(OH)2), magnesium oxide (MgO), magnesium carbonate (MgCO3). Equations listed in this invention may or may not be stoichiometrically balanced.

The term "water shift reaction," abbreviated as "WSR," also known as "water gas shift reaction" and abbreviated "WGSR" or "WGS," is defined by the equilibrium reaction CO+H2O with dynamic equilibrium with CO2+H2.

The term "non-equilibrium water gas shift reaction," abbreviated as "NEWGS," is a modified WGS that does not operate in equilibrium and promotes H2 formation by continually removing excess CO2, defined by CO+H2O→CO2+H2.

The term "Fischer-Tropsch reaction," abbreviated as "FT reaction" is a process currently known in the art which converts CO and H2 into liquid fuels, defined by H2+CO→liquid fuel+H2O. It is understood that the inventive creation of syngas can be further processed in an FT reactor as known in the art to create high-value biochemicals or biofuels.

The term "CO2 electrolysis" refers to the process of using electricity to split CO2 into CO and O2 and is defined by the reaction 2CO2+e-→2CO+O2.

The term "superomniphobic," as used herein, refers to super-repellant surfaces that display low contact angle hysteresis promoting easy roll off or bouncing of the contacting liquid droplets (Patent Literature (PL) 1 and 2). To create surfaces exhibiting superomniphobic properties, the surfaces have to display super-repellent features in terms of superhydrophobicity (contact angles >150°, contact angle hysteresis <5° with water) and superoleophobicity (contact angles >150°, contact angle hysteresis <5° with low surface tension, usually $\gamma_{LV}$<30 Nm/m$^2$, with liquids such as oils and alcohols).

The term "traditional top cycle," also known as "combined heat and power" or "CHP," describes any power generation cycle which generates electricity and waste heat. It may use a variety of fuels, including but not limited to natural gas or petroleum or fossil fuels. It typically includes a compressor, combustion chamber, and expander, as known in the art. It may include any configuration, including rotary ramjet engine.

The term "biomass drying process" describes any process used for removing water from biomass as a pretreatment step for further processing, usually within the biomass to liquid fuel conversion process, as known in the art.

The term "biofuel processing" to turning biomass into usable biofuel. The preferred embodiment used unprocessed biomass, which may or may not have high water content. The process is described by the following equation: biomass+H2→CO2+H2O+biofuel.

The term "biomass reaction," as used herein, refers to the integrated process of a non-equilibrium water gas shift reaction with biofuel processing. The integrated, co-located processing drastically increases the efficiency and allows for a process that minimizes or eliminates additional additives, such as methanol catalyst. As described previously, the NEWGS is described by the equation CO+H2O→CO2+H2. The CO2 is removed and used in processes as shown in the subsequent figures (or known in the art) in order to drive the forward H2 producing reaction. The H2 is then directly used within the biofuel process, which is described by the equation biomass+H2→CO2+H2O+biofuel. The biofuel can then be removed for further processing and/or distribution. The excess CO2 and H2O is then used as shown in subsequent figures or as known in the art. Unreacted syn gas is also often removed with the excess CO2. The term "O2 separation membrane" is a device known in the art that uses pressurized air to separate into depressurized O2 and pressurized N2 streams.

The terms "oxygen-enriched" and "oxygen-depleted" air refers to air having more or less oxygen, respectively, than expected levels in average incoming air. "Ambient air" is assumed to be approximately 20% oxygen and 80% nitrogen for ease of demonstration. Changes in design due to actual composition of ambient air is obvious to those knowledgeable in the art.

The term "fuel" is a chemical reactant that is exothermic during an oxidation reaction.

The term "soot" is a form of amorphous carbon particles and is used to yield a homogeneous highly radiative flameless combustion.

The term "recuperator" is a method of recovering waste heat downstream of an expander and transferring the thermal energy upstream of either a compressor, turbocompressor or pump.

The term "entrainment" refers to the practice of direct contact recuperator for a Brayton cycle by combining a portion of the high temperature engine exhaust with the incoming air flow to drastically increase the temperature of the incoming air. If the incoming air flow is oxygen enriched air, the entrainment of exhaust will dilute the incoming air to oxygen content equal to or slightly above standard atmospheric air, but less so than prior to dilution. It is possible, though unlikely appropriate, to dilute the incoming air to $O_2$-depleted air.

The term "pyrolysis" is used interchangeably with "decomposition" and refers to the decomposition of fuel, such as natural gas (i.e., methane) at elevated temperatures, described by the equation $CH_4 \rightarrow C+2H_2$ ($\Delta H_{1100K}$=77 kJ/kmol) in this embodiment. This elevated temperature is referred to as the "pyrolysis temperature". The pyrolysis temperature is different for different fuels and natural gas (methane) is used as an illustrative example but any fuel as obvious to those in the art could be used. The elevated temperature required is preferred above 700 C and particularly preferred above 1100 C in absence of a "decomposition catalyst" or between 400-700 C in the presence of a "decomposition catalyst" as known in the art.

DETAILED DESCRIPTION OF INVENTION

Here, as well as elsewhere in the specification and claims, individual numerical values and/or individual range limits can be combined to form non-disclosed ranges.

Exemplary embodiments of the present invention will now be discussed with reference to the attached figures. Such embodiments are merely exemplary in nature. With regard to the figures, like reference numerals refer to like parts.

Features of the System

The inventive system has multiple major features/properties, largely centered around optimizing the solvent use and conversion of lignocellulosic biomass into energy-dense and highly transportable fluid flows. The result is high-capital utilization factors, low greenhouse gas emissions, and maximum displacement of non-renewable energy sources amongst stationary and mobile assets typically within a sustainable community model. The major features and properties are:

1) very high energy density—the combination of the solvent, which is subsequently used as a liquid transportation fuel, with solids (though separate) of cellulose (preferably with reduced Van der Waals interaction between fibers by at least 10%, preferably at least 30%, and specifically preferred by greater than 90%) reduces the viscosity of the cellulose) and/or lignin 2) the transport system reduces the dust explosion risk by at least 10%, preferably at least 30%, and specifically preferred by greater than 90% as compared to the non-solvent carrier cellulose and/or lignin 3) the economic value of using a solvent for pretreatment of lignocellulosic material, such that the solvent fractionates the cellulose, hemicellulose, and lignin. Preferably the solvent is a fuel that is capable of being used within an internal combustion engine effectively equivalent or substitutable at least in part with a diesel, biodiesel (or even a gasoline). Particularly preferred such that the solvent is hydrophobic so as to separate from the water phase while maintaining solubility (or at least miscible) with the lignin. Particularly preferred such that the solvent also limits the cellulose interfiber hydrogen bonding during transport of the combined solvent-cellulose fluid so as to reduce bridging of fluid during pumping, and also yield a reduction in viscosity as compared to a cellulose-water fluid without the solvent.

4) utilization of the heat of vaporization, whether directly or via solvent recompression, within an effectively equivalent Rankine (at least the high-side pressure portion through expander) or Brayton cycle (if the solvent is to be utilized immediately as a fuel). The system efficiency is increased as the heat of vaporization is put to work for power generation, and not simply lost due to thermodynamic cycle irreversibility in the solvent-cellulose or solvent-lignin separation or concentration (of solid phase).

5) integration of a preferred alkaline (it is understood that acidic processes are anticipated as well) pretreatment process with the solvent, particularly preferred is ammonia in combination with the solvent so as to enable the precipitation of mineral ash from the biomass, to reduce or eliminate the contamination in the engine (as known in the art). This use of ammonia reacting with minerals enables a further reduction of cellulose interfiber bonding while also having the resulting precipitates or removal by ion-exchange (including an optimal resin-wafer electrodeionization process, as well as traditional electrodialysis) to be used as known in the art as a fertilizer. The further addition of ZnO "zinc oxide" also has the further ability to reduce interfiber bonding as recognized in the art.

6) Combining the solvent extraction with a gravity-driven hygro-responsive membrane separation substantially improves the biomass to biofuels conversion efficiency, particularly when the solvent is hydrophobic (i.e., non-polar). One such an embodiment is the extraction of butanol from a fermentation broth with an extractant having a high affinity to butanol (partition coefficient, k>1, preferably >2 and specifically preferred >2.7) as compared to ethanol (k≈0.65) and acetone (k≈0.2).

The particularly preferred embodiment uniquely has the following properties/feature: a) solvent is hydrophobic, b) solvent is capable of extraction from water by an extractant having a partition coefficient >2, c) solvent is a superior liquid transportation fuel either standalone or in combination with a solubilized or colloidal dispersion of a lignocellulosic solid constituent as compared to ethanol or methanol, d) solvent solubilizes lignin (and optionally and preferably maintains a stable colloidal dispersion with cellulose), e) solvent fractionates a solid lignocellulosic biomass into at least two constituent components, f) solvent enables cold temperature (e.g., less than 0 Celsius and preferably lower than −45 Celsius) transportation of a liquefied lignocellulosic biomass having at least one of the at least two constituents such that the liquefaction process takes place at temperatures lower than 350 Celsius (and preferably lower than 300 Celsius, and specifically preferred lower than 220 Celsius), g) solvent is preferably manufactured by fermentation of lignocellulosic biomass though alternatively from a petroleum-derived feedstock so as to enable particularly small-scale and modular processes to be cost-efficient, and h) solvent has a decomposition temperature greater than 200 Celsius so as to enable waste heat energy recovery to be utilized with electrical/mechanical transformation through either a Rankine or Brayton cycle and that the solvent is the thermodynamic working fluid. It is understood that the ideal solvent has all of the above properties/features (i.e., from (a) through (h)), but it is essential for the solvent to have at least three and preferably at least five of the aforementioned properties/features.

Further post liquefaction and fractionation of the lignocellulosic biomass processing including the aforementioned innovative features of post-processing (particularly for reactions that are at temperatures greater than decomposition temperature of the individual or aggregate fractionated biomass constituent) are virtually all enhanced due to more precise control of thermal balance achieved due to the significantly higher surface area of solid fractionated biomass constituent such that the chemical reaction (whether it be oxidation, hydrogenation, combustion etc.) takes place at a rate that is at least 20% faster than a non-fractionated solid lignocellulosic biomass (and preferably at least 50% faster, and specifically preferred at least 200% faster). The reaction takes place for the aggregate within each individual fractionated constituent at approximately the same time and at approximately the same temperature as a method to reduce tar or char formation by at least 20% (and preferably at least 50% lower, and specifically preferred at least 80% lower) as compared to the same reaction under otherwise identical conditions (i.e., temperature, pressure, flow rate, etc.) for non-fractionated solid lignocellulosic biomass whether it be in a solid or liquefied form.

It is understood that the cellulose can be depolymerized to varying degrees, as known in the art, such that the cellulose having reduced interfiber bonding due to the solvent presence will maintain a stable colloidal dispersion in the solvent. Since the cellulose in this invention is often utilized in a secondary process at a different location than where the biomass is fractionated into the cellulose, hemicellulose, and lignin components, a primary objective is to enable the cellulose to be easily transported in a pump-able slurry, to reduce subsequent interfiber hydrogen bonding during transport to the secondary process location, and to reduce the dust explosion potential (especially when the solvent, particularly n-butanol or sec-butanol) creates nanofibrils of cellulose having significant surface area.

It is further understood that one of the most important secondary processes, especially in a world that is rapidly increasing towards electric vehicles, is the production of electricity. Biomass is inherently an energy storage method such that biomass to electricity is a perfect complement to intermittent renewable energy sources. However, the traditional biomass to electricity is a biomass boiler/fluidized bed that is to date economical at very large scale and even then, is not suited to ultra-high efficiency combined cycle. Such traditional biomass to electricity plants DO NOT enable very rapid response (i.e., less than 10 minutes, or even more preferred less than 1 minute) electricity so as to provide frequency regulation or load-matching power generation profiles intermingled with the intermittent renewable energy sources. Therefore, it is an object of the invention to utilize minimally processed solid biomass components that are suitable for direct operation in an internal combustion engine, a micro-turbine, a small-scale rapid response gasifier for subsequent combustion in a turbine (or micro-turbine), or in a recuperated power generation cycle yet leveraging liquid handling methods (e.g., pump). The rapidly declining renewable energy prices demand that fuel-consuming power generation MUST have a low-cost fuel source, and energy superior energy efficiencies through combined cycle operations. The waste heat, from the radiated energy of an internal combustion engine "ICE" is sufficient to evaporate the solvent from the cellulose or lignin, which can then be superheated from the internal combustion engine exhaust waste heat. The reduced bonding between cellulose interfibers, the use of the solvent as a fluid carrier, and the relatively low boiling point are ideally suited to enable a combined cycle ICE system. The very high surface area of the cellulose also enables rapid combustion. In fact, the cellulose fiber post-solvent removal can be added with water (though preferably immediately prior to combustion i.e., less than 5 minutes, particularly preferred at less than 1 minute so as to minimize subsequent hydrogen bonding between cellulose fibers) so as to operate in a manner similar to coal-water slurries as known in the art. However, the inventive colloidal dispersion of cellulose has virtually no sulfur and no minerals to respectively significantly enhance combustion emissions and reduce corrosion and/or abrasion resulting from mineral deposits. The cellulose, whether partially hydrolyzed by water or a butanol-cellulose complex, enhances the lubricity within the ICE that has the benefit of reducing friction and therefore increasing energy efficiency.

It is further understood that a secondary process anticipated in the scope of this invention can include virtually any process as known in the art for post-transformation of pyrolysis oils, petroleum derived crude oil (including distilled fractions, or reacted fractions). These include known process intensification methods such as supercritical processing/reactions, cavitation, or pressure reactions within a twin-screw extruder. Each of these secondary processes will achieve superior results when utilizing the more homogeneous fractionated constituent of the lignocellusic biomass via the inventive process prior to the post processing as known in the art of the aforementioned secondary processes.

This process leverages the solvent as a critical carrier of lignin, as lignin as a powder or solidified lignin respectively has handling issues plus explosiveness if lignin is isolated.

The solvent is preferably a hydrophobic solvent including solvents selected from the group of n-butanol and methyl butenol "MBO". Additional solvents are anticipated, though not preferred as they are miscible with water, which include ethanol and tetrahydrofuran "THF". In the latter instances, the removal of water from the THF solution requires evaporation/distillation of THF first which yields precipitation of lignin within the remaining water solution. Therefore, the evaporated THF will have to be added to the then dried precipitated lignin to solubilize the lignin in order to enable the lignin to be in a liquid pump-able slurry or solution for transport to the power generator location. Solid lignin, particularly in a powder form is recognized as having significant dust explosion potential.

The hydrophobic solvents are preferred liquid fuels within transportation vehicles within the context of fuel spillage and also significantly lower energy costs in the separation of the solvent from water, as compared to the aforementioned water-miscible solvents.

The use of the solvent, which is a preferred fuel for transportation vehicles also maximizes the value extracted by the combined operation as liquid transportation fuels are more valuable than electricity.

Furthermore, the waste heat of electricity production is recovered for further electricity production enabling the solvent heat of vaporization to contribute to the total system efficiency.

This process leverages the solvent to fractionate the biomass, while removing the mineral ash. The fractionated biomass into separate components, particularly the solid components (e.g., cellulose, lignin), are ideally particle-size reduced for homogeneous mixing with metal oxide and metal ferrite for low-char and low-tar gasification. Importantly the fractionated biomass enables more precise control of any secondary process as each fraction has different time domains in terms of its chemical disassociation. The very high surface area, and very high-dispersion of the cellulose/lignin enable rapid gasification with virtually no thermal lag due to otherwise insulative properties of lignocellulose. The preferred embodiment creates a superior syngas, as known in the art, to enable superior secondary reactions e.g., FT reactions to create biochemical and/or biofuels.

In a similar manner as the above mixing with metal oxide or metal ferrite powders, the very high surface area, and very high-dispersion of the cellulose/lignin enable superior thermocatalytic reactions including water-gas-shift reactions. One such embodiment is the further combination of metal oxide, preferably $Mg(OH)_2$ and methanol with the resulting cellulose or lignin (but in separate reaction streams, as the decomposition/reaction rates are NOT identical) and copper catalyst. The reaction rate and ability to homogeneously (i.e., having an energy density and/or mass density variation of less than 20%, though preferably less than 5% throughout the mixture) mix the cellulose or lignin with the catalyst and Mg(OH)2 and methanol enable an enhanced water-gas-shift reaction as the Mg(OH)2 will react with the resulting CO2 so as to enhance the production of more hydrogen. The ability to have all reactants and catalyst in a cross-flow manner enables a reduction of methanol so as to minimize the use of fossil fuels in liquefying the cellulose or lignin into a liquid fuel. The separation of cellulose and lignin, and removal of mineral ash (which is also a catalyst contaminant) is vital to the commercialization of the lignocellulosic conversion into a liquid transportation fuel (such as mixed alcohols as known in the art). The commercial viability of this approach is significantly superior when the biomass is fractionated and made into a pump-able slurry or solution when the solvent is removed with minimal distillation energy requirements. The particularly preferred embodiment utilizes a hygro-responsive membrane so as to separate the polar and non-polar components (i.e., water with dissolved hemicellulose sugars respectively with lignin dissolved in solvent e.g., n-butanol). Prior art systems require expensive distillation columns, with the expense being both capital expenditures and operating energy costs. The specifically preferred embodiment utilizes a hydrophobic solvent that does not break-down or change into a chemical with less lignin solubilizing power, notably n-butanol or MBO, or even sec-butanol. Though isobutanol can also be used, it doesn't have the superior hydrophobic features of n-butanol or MBO. A further addition to the solvent, notably for the purpose of enhancing the separation of polar and non-polar phases includes the unique category of hydrophobic ether solvents and particularly of note is cyclopentyl methyl ether "CPME". CPME is of particular note as it functions in a similar manner to tetrahydrofuran "THF" but importantly CPME is hydrophobic whereas THF is entirely miscible with water. CPME, as opposed to n-butanol has the disadvantage of cost, non-renewable, and not currently suitable as a transportation liquid fuel (even if the cost disadvantage could be eliminated, though not likely). CPME, or combinations of CPME with n-butanol or MBO gains the otherwise advantages as known in the art of THF in terms of lignocellulosic fractionation and liquefaction.

Implementing the fractionated biomass components, having a free-flowing capability, enables counter-flow that is particularly important in any heat recovery methods, or precise control of thermal conditions in which any reaction chemistry takes place. The solvent system has a viscosity sufficiently low so as to enable counter-flow heat recovery heat exchangers, an important aspect in optimizing energy efficiency. The solvent system has a particle size, for non-solubilized components such as cellulose, such that the solvent system can be optimized by processing in process intensification equipment (notably twin-screw system having integral reaction chambers and injection ports, such that a heated solvent or solvent-water solution can have direct injection (so as to minimize or eliminate electric-resistive heating elements) of the lignocellulosic biomass (preferably with recovered waste heat directly, or waste heat that undergoes recompression through either a compressor or heat pump). The high-shear of the twin-screw, as known in the art, accelerates the fractionation time required for breaking down the lignocellulosic material into the distinct components e.g., lignin, cellulose, hemicellulose for further processing into the hygro-responsive membrane to partition without any additional thermal energy into a first polar phase and a second non-polar phase.

Turning to FIG. 1, FIG. 1 depicts the process flow of the biomass fractionation and liquefaction process at a first location (indicated by process blocks outlined in non-bold weight), and the distributed power generation w/ integral liquid transportation fuel depot process at a second location (indicated by process blocks outlined in bold weight). Biomass 280, which is a lignocellulosic biomass, that is processed with solvent 210.2 as recycled from downstream of the solvent condenser 140 (though not preferred, as this would involve "round-trip" logistics) or downstream of the polar & non-polar membrane 260 (i.e., hygro-responsive membrane) as a preferred process. The solvent can be isolated from the otherwise dissolved lignin by evaporation or distillation through the heat exchanger 200.2 (though this is more energy and capital intensive, however evaporated solvent can transfer thermal energy by way of direct injection into the biomass to accelerate the biomass fractionation process). Another option, which is energetically preferred is to pass through the solvent-lignin rich solution a nano-filtration 201 membrane yielding the solvent for recycling and a lignin with a significantly reduced solvent volume (if any remains) so as to maintain a reduced risk of dust explosion of the resulting lignin fraction.

The at least partially liquefied biomass 280 continues on, as known in the art, to a solids filter 210 so as to isolate the non-dissolved cellulose 200 for further processing. The cellulose is ideally remaining in a solid-rich colloidal dispersion such that interfiber bonding is reduced due to the presence of the solvent. The solids filter removes mineral ash 202 precipitates as a result of solution neutralization. Downstream of the solids filter 210, the solubilized combination is in fluid communication with the polar and non-polar membrane 260 (i.e., hygro-responsive membrane) so as to fractionate the liquefied biomass solution (i.e., lignin rich with solvent plus any residual water 250, and dissolved sugar rich with water 220). Though the remaining water in the solvent-lignin solution is expected to be negligible, and optional process step as known in the art can be exploited to remove water 230. Post-processing of hemicellulose w/ water 220 can range from dewatering, conversion via fermentation to a wide range of materials though preferably as known in the art to additional quantities of solvent in which another instance of the hygro-responsive membrane enables energetically favorable separation of solvent from water. It is a fundamental aspect of the invention such that the solvent management system manages and controls the production of solvent, distribution of solvent, and the recycling of the solvent. Within the context of a sustainable community, particularly one with significant renewable energy and electric vehicles for mobility, has a reduced demand for solvent (or alternative liquid transportation fuels such as ethanol), therefore the conversion of sugars from hemicellulose can be used in secondary processes as known in the art to create higher-value add products such as proteins for food consumption or polyphenols through microalgae production. In this instance, it is best that the biomass fractionation and liquefaction process maximizes the recycling the solvent for ongoing solvent inventory within the liquefaction process which then requires the solvent-lignin solution to have a significant amount of solvent removed so as to create a lignin-rich concentrated solution. The preferred embodiment in this instance maximizes the lignin to solvent ratio so as to maintain the lignin-rich solution as a pump-able liquid so as to reduce the transport costs and the risk of dust explosion.

In the instance where the demand for electricity in a distributed environment is less sustainable it is advantageous for the solvent management system to maximize the transport of fractionated biomass solids (preferentially lignin due to solvent solubility and energy density) to a distributed power generation facility. Continuing on with this instance, especially when there is a significant demand for a liquid transportation fuel, it is optimal for the solvent to be maximized towards the combustion of the solvent in mobile vehicles 40 (which has a significantly higher value, of at least 20% and in most instances at least 50% more value) as compared to the value of electricity on an value per delivered energy basis. The lignin with solvent 70 (i.e., lignin-rich solution) passes through a heat exchanger 200.1 so as to evaporate at least a partial quantity of the solvent (as indicated by the "+" therefore becoming lignin with solvent (−) 190 as a fuel for the electricity production generator 10 (being advantageous as this lignin-rich solution is energy-rich, pump-able and capable of being atomized as known in the art preferably by ultrasonic nozzle or electrostatic nozzle enabling the very important feature of a combined cycle power generation cycle as compared to the traditional biomass power plant being a simple cycle with lower efficiencies therefore requiring at least 50% more biomass per unit of electricity produced.

The evaporated vapor is then utilized in itself as a bottom cycle power generator through an expander for additional electricity 150 (as known in the art) and then subsequently condensed in the solvent condenser 140 such that the solvent is then utilized within mobile vehicles as a transportation fuel 40. The resulting electricity from either the bottom-cycle expander 150 is optimally directed to a flow battery electrolyte 160 (which is preferably a flow battery system such that the charging of the electrolyte yields a rich source of oxygen for a wide range of purposes though preferably for on-site gasification of at least one of the fractionated solid biomass (e.g., cellulose or lignin). The waste heat from the production of electricity 170 by the generator combustion of solvent depleted lignin-rich 10 solution can be used for the evaporation of the solvent (as already described) through waste heat exchanger 180.2 or directed to 180.1 for any co-located industrial process including (if on-site) the biomass liquefaction/fractionation process. The resulting electricity 170 is optimally used, from a sustainable community perspective into charged electrolyte for a flow battery as it is more cost effective to perform CO2 sequestration at the power generation plant as compared to fuel consumption in each and every vehicle that consumes CO2 producing fuel 40.

Figure 2:
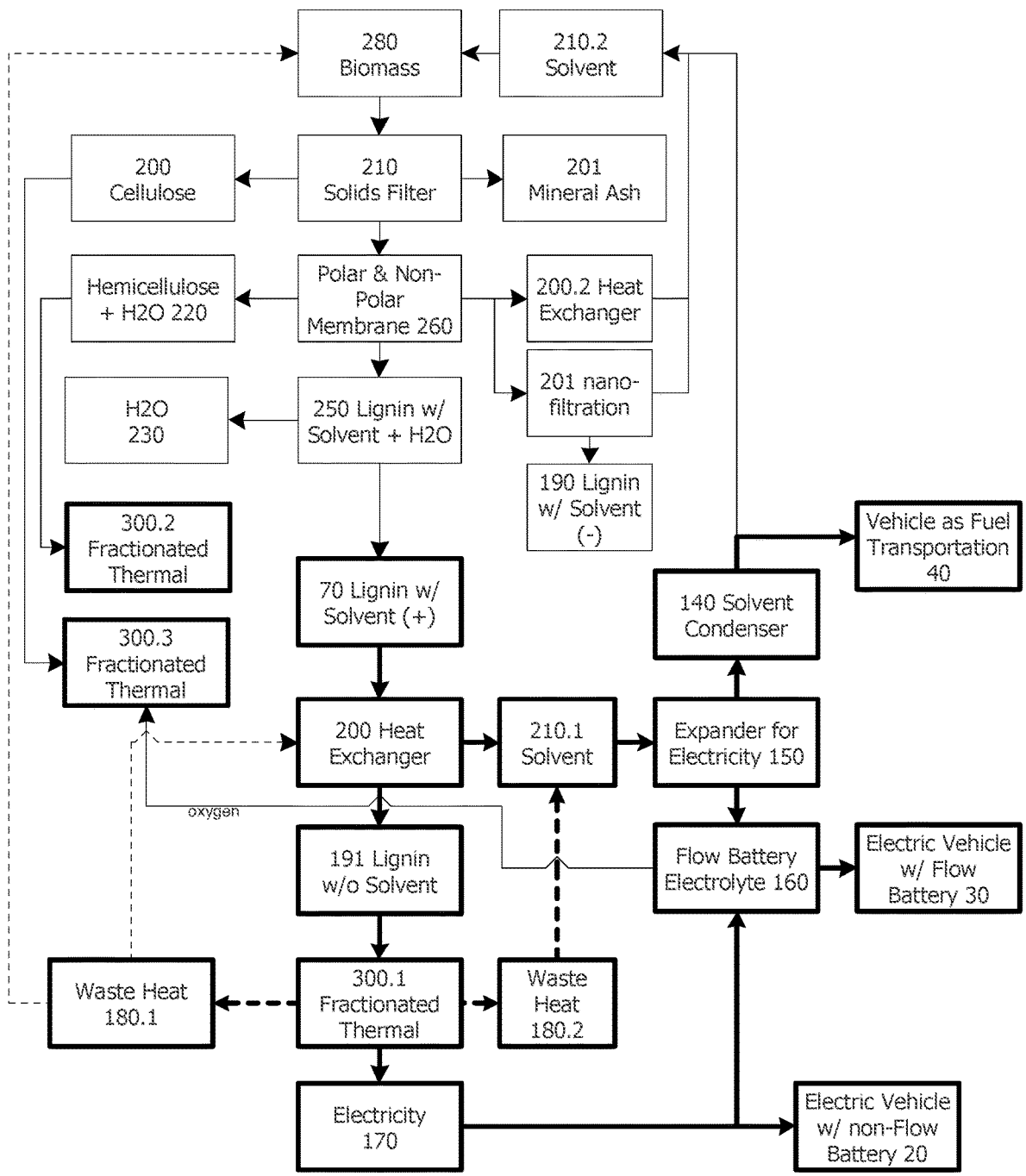
FIG. 2 is a flow chart detailing the system from a solvent centric perspective within a distributed environment, such that the biomass liquefaction and fractionation process is at a central location and at least a partial solvent separation takes place within a secondary process such that at least two of the fractionated constituents are processed in parallel and distinct operations.

Turning to FIG. 2, FIG. 2 is virtually identical to FIG. 1 with the following differences. In this embodiment, the at least two components fractionated from the original lignocellulosic biomass of cellulose and/or hemicellulose (or co-products resulting from fractionation/liquefaction process e.g., sugars) are individually thermally processed so as to minimize the creation of char or tar by at least 10% (and preferably by at least 90%) in its thermal decomposition process. One embodiment is thermal decomposition by way of gasification (as known in the art), though preferably with the addition (though not shown) of metal oxide and/or metal ferrite to enhance the gasification process in the creation of enhanced syngas. It is a critical feature of the invention such that the surface area of the fractionated solid biomass is increased by at least 10% and preferably greater than 200% so as to virtually eliminate the otherwise insulative (and non-homogeneous) properties of the biomass which yields undesirable byproducts such as char and/or tar. Though other derivatives exist (not shown), this embodiment depicts the hemicellulose with water (or subsequently processed to concentrate the hemicellulose or its co-products) 220 going into a thermal decomposition process 300.2 as indicated by fractionated thermal process (e.g., gasification for syngas, and then further optional processing such as FT processes to create biochemical or biofuels); and/or likewise for cellulose 200 into a separate and individual fractionated thermal process 300.3. As noted in FIG. 1, the oxygen generated by the charging of flow battery electrolyte is optimally used in this aforementioned gasifier. It is understood that the oxygen source can be used in any of the fractionated thermal processes (300.1, 300.2, and/or 300.3).

Figure 3:
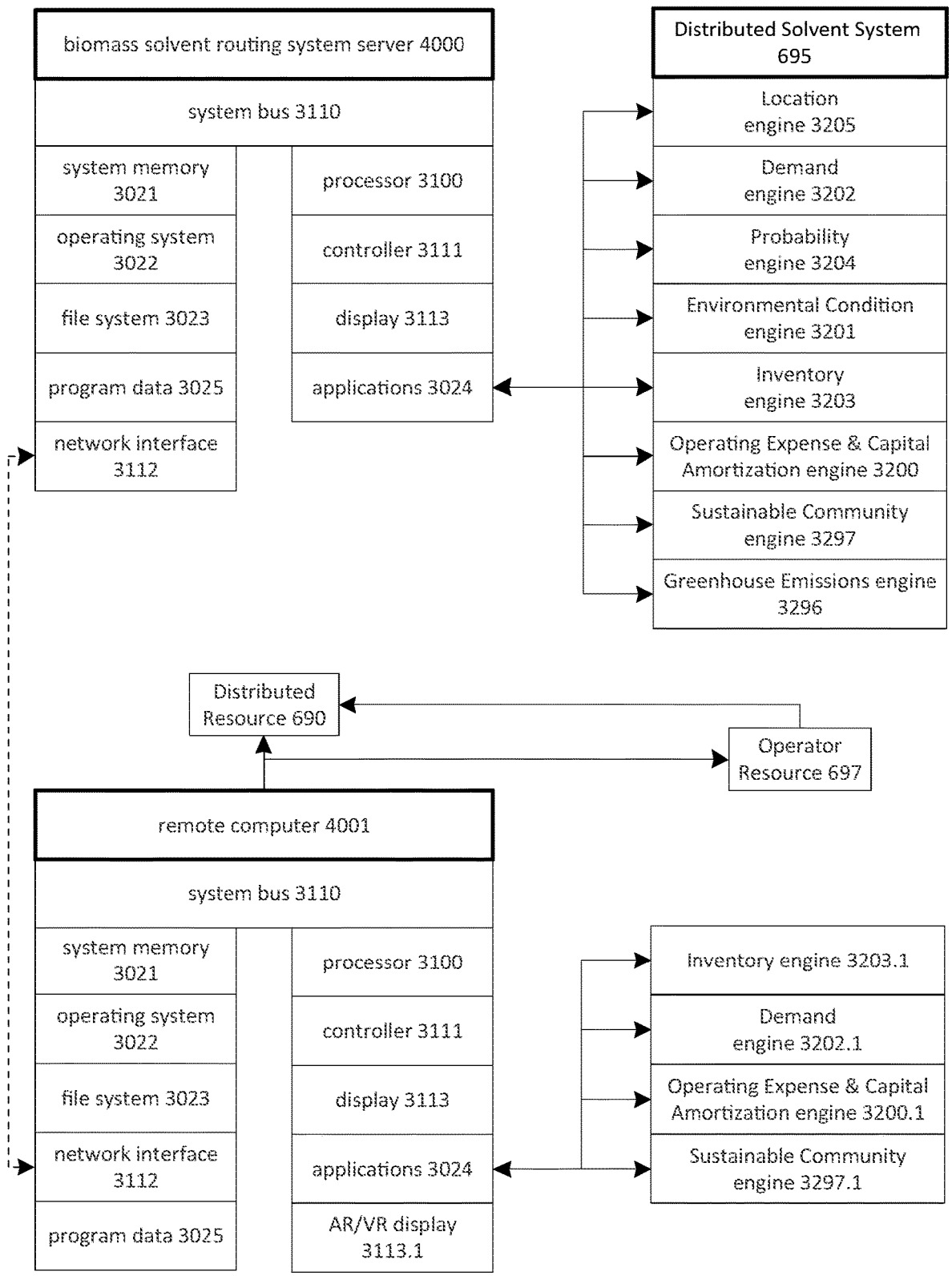
FIG. 3 is a chart detailing the major hardware and application programs for the management of virtually all aspects of solvent flow including scheduling of solvent use, logistics to meet those solvent use requirements, and also optimizing solvent use for reduced greenhouse gas emissions.

Turning to FIG. 3, FIG. 3 depicts the solvent management and control system that coordinates every aspect of the solvent from production, fluid transfer, transport to a distributed (and secondary site for utilization in methods as depicted in FIGS. 1 and 2), and sales for subsequent secondary purposes that optimizes on various functions ranging from return on capital investment, minimization of operating expenses, maximization of revenue generation, and/or minimization of greenhouse gas emissions of the collective biomass to biofuel (and solvent) consumption. This biomass solvent routing system "BSRS" has a server 4000 that orchestrates the entire process. The BSRS has a system bus 3110 to perform hardware aspects of implementation as known in the art by leveraging system memory 3021 by way of control by an operating system 3022 through a file system 3023. Within the file system is program data 3025, such as a database of a preferred object-oriented architectural structure, using an on-board (though it is recognized that this function can take place remotely via the "Cloud" computational and communication resources. The system bus 3110 coordinates programming instructions through a processor 3100 and its controller 3111, with inputs and outputs respectively managed by operating personnel often via displayed 3113 user-interface screens "GUI" in accordance to applications 3024 that comprise components from rules-based engine to machine learning. It is further understood that this architecture is often repeated at a distributed resource 690 (i.e., remote) located within the distributed nature of the solvent centric BSRS system. Communications take place through the network communications interface 3112 and can further be communicated via user interaction methods including augmented reality or virtual reality display 3113.1 for an operator resource 697. The application rule-based engine specifically for distributed solvent system 695 is comprised of a series of sub-engines that contain the management of system objects ranging from production equipment, logistics equipment, power generation equipment, to transportation vehicle equipment and all of the necessary storage tanks to buffer inventory management of the solvent, whether the solvent is standalone (i.e., pure) or solution (e.g., lignin-rich solvent solution) or colloidal dispersion (e.g., cellulose fiber-rich solvent) or blended with additional fuel components (e.g., biodiesel, ethanol, gasoline, diesel, etc.) to make a "completed" liquid transportation fuel to meet the specifications for a subset of transportation vehicle equipment fuel requirements. It is understood that hereinafter a reference to solvent as "Solvent" inherently interchanges between the aforementioned forms in which the solvent is present. The location engine 3205 maintains all location-specific equipment, control parameters, sensor inputs, control outputs, and inventory control of the Solvent. The location engine 3205 rules center around logistics between the lignocellulosic pretreatment site and all distributed resources within the distribution chain of the Solvent, including location-specific data for parameters as shown in FIG. 4 as well as known in the art parameters specific to the operations of processes including electricity power generation notably power production efficiencies, demand profiles, etc. A particularly important parameter used with the location engine is the temperature profile (containing both historic and projected as established by the environmental condition engine 3201) in which the Solvent will be exposed to, as the mass percentage of solvent within the Solvent fluid has a direct impact of viscosity (which is a function of temperature). The demand engine 3202 has the application code and rules-based engine specific to calculations based on historic data and projected date, including the data manipulation as performed by machine learning (as known in the art) so as to accurately establish at each location the demand profile of Solvent as a function of time. The probability engine 3204 utilizes the demand profile of Solvent in combination with statistical probability analysis, including machine learning algorithms, to provide an adjusted demand profile of Solvent. The inventory engine 3203 integrates best practices based on the adjusted demand profile in combination with both real-time inventory of Solvent plus the tank buffering capacity as maintained by each individual sustainable community within its respective sustainable community engine 3297 (as each community best understands unique aspects of Solvent demand and importantly due its accountability and responsibility must have the means to alter Solvent transport decisions). The distributed solvent system 695 within the context of the overall BSRS 4000 takes into account the operating expense and capital amortization engine 3200 to finalize the Solvent production, transport, and distribution; and most importantly to make determinations of how the Solvent is used, converted, distributed and ultimately consumed taking into account variations between fixed and variable pricing means on a real-time basis (i.e., in other words there are periods of time in which spare manufacturing capacity such as for solvent manufacturing with ample supply of cellulose would lead to the decision of manufacturing via fermentation additional solvent even if it impacts a deterioration of sales price). Lastly, the total economics of operation includes the impact of greenhouse gas emissions as monitored and calculated by the greenhouse emissions engine 3296 as every sustainable community is particularly interested in comprehensive cost (i.e., take into account CO2 emissions, taxes associated with GHG emissions or benefits realized by avoided GHG emissions, etc.). Virtually every connected distributed resource 690, which optionally has an operator resource 697 monitoring and potentially altering system decisions, therefore each location has its own representation of control parameters plus remote computer 4001 applications that are represented by the application engine.dot.instance (e.g., "3203.1"). It is understood that the location instance representation can be co-located, in the Cloud, or in fact within the server 4000 operating as specific location instance.

Turning to FIG. 4, FIG. 4 is a subset of parameters with an understanding that each parameter and/or subset of parameters are linked to a specific physical or virtual object as represented by its object id. "F(t)" indicates that the parameter is a function of time, such that in most instances the combination of historic data and projected data provide the variability of the parameter over the relevant time domain. Each parameter is inherently understood as noted within FIG. 4 (so no repetition is necessary, but rather understood to be listed individually within the specification and specifically within this paragraph), except for the following:

Biomass decomposition temperature is the temperature in which that fractionated or non-fractionated biomass begins a chemical transformation (most notably breakdown, such as hemicellulose to furfural);

Transport projected temperature is the temperature or temperature profile f(t) as Solvent moves from a first location to a second location (i.e., destination);

The Solvent has multiple physical parameters of importance including viscosity, boiling point, melting/freezing point, solubility, energy density, mass density, etc. These same parameters are also relevant for each of the biomass fractionated constituents and collectively referred to as biomass fractionation parameters;

Production equipment parameters include all relevant data in terms of calculating financial data such as amortization rates and operating costs, as well as operating capacity. Storage tanks as well as other inventory buffering equipment is inclusive of production equipment; and Logistics equipment parameters is approximately identical to production equipment parameters, though with known in the art variability of parameters as a result of the operational task executed.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A solvent fractionation method liquefying a solid lignocellulosic biomass with a solvent and then a solvent combustion process using the solvent as a liquid transportation fuel within a mobile vehicle comprising: liquefying a solid lignocellulosic biomass using the solvent at a temperature less than 350 Celsius, fractionating the solid lignocellulosic biomass into an at least two constituent components whereby a lignin fraction is a first component of the at least two constituent components, solubilizing the lignin fraction or maintaining a colloidal dispersion of the lignin fraction with the solvent from the biomass liquefaction process through the transport of the lignin fraction to an integrated power generator fueled by a portion of the lignin fraction and whereby the integrated power generator produces a resulting electricity and a resulting waste heat, and the waste heat of the integrated power generator fractionates at least 10% on an energy basis of the solvent out of the solubilized lignin fraction or the colloidal dispersion of the lignin fraction and wherein the at least 10% of the solvent is used for combustion in the mobile vehicle.

2. The solvent fractionation method according to claim 1 whereby the first biomass liquefaction process using the solvent is further comprised of a step for removing a mineral component from the solid lignocellulosic biomass and whereby the removing of the mineral component is by precipitation or an electrodialysis ion removal process from the liquefied solid lignocellulosic biomass.

3. The solvent fractionation method according to claim 1, whereby the fractionating of the solid lignocellulosic biomass into an at least two constituent components has a cellulose fraction and the cellulose fraction is comprised of a cellulose fibers, and the solvent reduces an at least 10% reduction of hydrogen bonding between the cellulose fibers resulting from a solvent-cellulose interaction process.

4. The solvent fractionation method according to claim 1, further comprising a gasifying step whereby the at least two biomass constituents are gasified in a separate gasifier for each of the at least two biomass constituents such that each of the separate gasifiers operates at temperature above a decomposition temperature of each of the respective at least two biomass constituents.

5. The solvent fractionation method according to claim 1, further comprising an evaporation step whereby the at least 10% on an energy basis of the solvent removed prior to the combustion of the at least fractionated solid biomass and whereby the solvent removed has a heat of evaporation, and whereby the solvent heat of vaporization from the evaporated solvent increases the energy efficiency of the integrated power generator whereby the integrated power generator is operating a Rankine thermodynamic cycle with the solvent as a thermodynamic working fluid within the Rankine thermodynamic cycle.

6. The solvent fractionation method according to claim 5, whereby the Rankine or Brayton thermodynamic cycle is further comprising of an expander and a condenser for evaporating the solvent out of the solubilized lignin fraction or the colloidal dispersion of the lignin fraction, whereby the condenser is downstream of the expander condensing the solvent.

7. The solvent fractionation method according to claim 5, is further comprising a compression step by a compressor of the solvent out of the solubilized lignin fraction or the colloidal dispersion of the lignin fraction.

8. The solvent fractionation method according to claim 5 whereby the evaporation step has an upstream further atomizing step by an atomizing nozzle of an ultrasonic or electrostatic type, and whereby the atomizing nozzle increases a phase separation of the fractionated solid biomass slurry or solution into a solvent phase and a cellulose or lignin phase.

9. The solvent fractionation method according to claim 8, further comprising a mixing step whereby the solubilized lignin fraction or the colloidal dispersion of the lignin fraction is mixed with a metal oxide or a metal ferrite becoming an integral oxygen source and a solid composite fuel for combustion in a combustion step of the integrated power generator fueled by the portion of the lignin fraction in the solid composite fuel.

10. The solvent fractionation method according to claim 9 wherein the combustion step occurs at a temperature greater than 200 Celsius.

11. The solvent fractionation method according to claim 1 further comprising a mixing step combining the lignin fraction with a metal oxide or a metal ferrite and the combined lignin fraction with the metal oxide or the metal ferrite is a solid composite fuel slurry with an integral oxygen source as a first oxygen source.

12. The solvent fractionation method according to claim 11 is further comprising a heating step wherein the combined lignin fraction with the metal oxide or the metal ferrite is heated to a temperature greater than a solvent vaporization temperature of at least 150 Celsius and a temperature lower than an oxygen release temperature of at least 200 Celsius.

13. The solvent fractionation method according to claim 12 wherein the heating step separates a resulting solvent vapor through an omniphobic porous matrix leaving behind the omniphobic porous matrix the lignin fraction and the metal oxide or metal ferrite in a solid powder form.

14. The solvent fractionation method according to claim 1 further comprising a power generating step wherein the integrated power generator generates electricity, a charging step whereby the electricity is used to charge a flow battery having an electrolyte that releases an oxygen gas when the flow battery electrolyte is being charged, and a combustion step whereby the oxygen gas is consumed in the combustion process of by the integrated power generator to generate a resulting electricity.

15. The solvent fractionation method according to claim 14, whereby the combustion step consumes the oxygen gas released the charging of the flow battery electrolyte and by combusting the lignin fraction, after a mixing step of combining the lignin fraction with a metal oxide or a metal ferrite, into a syngas.

16. The solvent fractionation method according to claim 15, whereby the combustion step occurs for the first of the at least two constituent components and a second of the at least two constituent components individually and in an at least two gasifiers to reduce the creation of a tar or char residue by at least 50% as compared to the process of combusting the first of the at least two constituent components and a second of the at least two constituent components together within an individual gasifier.

17. The solvent fractionation method according to claim 1, whereby the solubilizing the lignin fraction or maintaining the colloidal dispersion of the lignin fraction with the solvent from the biomass liquefaction process through the transport of the lignin fraction to the integrated power generator fueled reduces a dust explosion potential by at least 10% lower the lignin fraction void of the solvent.

18. A solvent fractionation method using a first biomass liquefaction process using a solvent and then a solvent combustion process using the solvent as a liquid transportation fuel within a mobile vehicle comprising: liquefying a solid lignocellulosic biomass using the solvent at a temperature less than 350 Celsius, fractionating the solid lignocellulosic biomass into an at least two constituent components, whereby a lignin fraction is a first component of the at least two constituent components and then solubilizing the lignin fraction or maintaining a colloidal dispersion of the lignin fraction with the solvent from the biomass liquefaction process, whereby a cellulose fraction is a second component of the at least two constituent components, solubilizing the cellulose fraction or maintaining a colloidal dispersion of the cellulose fraction with the solvent from the biomass liquefaction process, followed by a transportation step of at least one of the lignin fraction with the solvent or the cellulose fraction with the solvent by a mobile vehicle to an integrated power generator fueled by at a portion of at least one of the lignin fraction with solvent or the cellulose fraction with the solvent, followed by a combustion step to produce electricity and waste heat by the integrated power generator.

19. A solvent fractionation method using a first biomass liquefaction process using a solid lignocellulosic biomass and a solvent at a liquefaction temperature less than 300 Celsius and then a second power generation process producing electricity and harvesting waste heat from the power generation process and then a third waste heat power generation process producing additional electricity by utilizing the solvent within a waste heat recovery process from the power generation process using the solvent as a working fluid in the waste heat recovery process whereby the solvent has at least three features selected from the group of features including: the solvent is hydrophobic; the solvent is capable of extraction from water by an extractant having a partition coefficient greater than 2; the solvent is a liquid transportation fuel either standalone or in combination with a solubilized or colloidal dispersion resulting from the biomass liquefaction process of the solid lignocellulosic biomass; the solvent solubilizes a lignin fraction from the lignocellulosic biomass; the solvent fractionates the solid lignocellulosic biomass into at least two constituent components whereby the first of the at least two constituent components is in a polar phase and the second of the at least two constituent components is in a non-polar phase; the solvent enables a transporting process by a mobile vehicle of at least one of the at least two constituent components at a temperature lower than −45 Celsius; the solvent is manufactured by at least one fermentation process from an at least one constituent fraction from the solid lignocellulosic biomass; and the solvent has a decomposition temperature greater than 200 Celsius.

* * * * *